US007163677B2

(12) United States Patent
Li et al.

(10) Patent No.: US 7,163,677 B2
(45) Date of Patent: *Jan. 16, 2007

(54) CATIONIC POLYMERS HAVING DEGRADABLE CROSSLINKS

(75) Inventors: Sheng Li, Vista, CA (US); Chris Castell, San Diego, CA (US); Sang Van, San Diego, CA (US)

(73) Assignee: Nitto Denko Corporation, Osaka (JP)

( * ) Notice: Subject to any disclaimer, the term of this patent is extended or adjusted under 35 U.S.C. 154(b) by 241 days.

This patent is subject to a terminal disclaimer.

(21) Appl. No.: 10/692,573

(22) Filed: Oct. 24, 2003

(65) Prior Publication Data

US 2005/0089503 A1    Apr. 28, 2005

(51) Int. Cl.
*A61K 31/74* (2006.01)
*A61K 47/48* (2006.01)
*A61K 31/7088* (2006.01)
*C08F 290/14* (2006.01)
*C08G 63/48* (2006.01)
*C08G 63/91* (2006.01)

(52) U.S. Cl. .................. 424/78.17; 514/44; 525/50; 525/54.1; 525/54.2

(58) Field of Classification Search ............... None
See application file for complete search history.

(56) References Cited

U.S. PATENT DOCUMENTS

| 6,159,591 | A | 12/2000 | Beihoffer et al. | |
| 6,290,947 | B1 | 9/2001 | Fitzpatrick et al. | |
| 6,379,966 | B1 * | 4/2002 | Monahan et al. | 435/455 |
| 6,696,038 | B1 | 2/2004 | Mahato et al. | |
| 6,878,374 | B1 * | 4/2005 | Yu et al. | 424/178.1 |
| 2005/0049387 | A1 * | 3/2005 | Van et al. | 528/272 |

FOREIGN PATENT DOCUMENTS

| EP | 1 279 682 A | 1/2003 |
| WO | WO 97/45069 | 12/1997 |
| WO | WO 99/22770 | 5/1999 |
| WO | WO 03/082316 | 10/2003 |

OTHER PUBLICATIONS

International Search Report for International Application No. PCT/US2004/033122 mailed on Feb. 14, 2005.
A. Kabanov, Pharm. Sci. & Tech. Today, 2 (9), 1999, 365-372.
B.M. Jeong, D.S. Lee, Y.H. Bae, S.W. Kim, Nature 388, 1997, 860-862.
B.M. Jeong, Y.K. Choi, Y.H. Bae, G. Zentner, S.W. Kim, J. Controlled Release 60, 1999, 109-114.
Boussif, O., Lezoualc'h, F., Zanta, M. A., Mergny, M. D., Scherman, D., Demeneix, B., and Behr, J.-P. Proc. Natl. Acad. Sci. USA 1995, 92, 7297-7301.
C-H. Ahn, S.Y. Chae, Y.H. Bae, S.W. Kim, J. Controlled Release, 80, 2002, 273-282.
Curiel, D. T., Agarwal, S., Wagner, E., Cotton, M. Proc. Natl. Acad. Sci. USA 1991, 88, 8850-8854.
Feng Liu and Leaf Huang, Journal of Controlled Release, vol. 78, 1-3, 2002, pp. 259-266.
Haensler, J., and Szoka, F. C., Jr. Bioconjugate Chem. 1993, 4, 372-379.
Henrik R. Ihre, Omayra L. Padilla De Jesus, Francis C. Szoka, Jr. and Jean M. J. Frechet, Bioconjugate Chem. 2002, 13, 443-452.
J.-S. Remy, B. Abdallah, M. A. Zanta, O. Boussif, J.-P. Behr, B. Demeneix, Adv. Drug Delivery Rev. 30, 1998, 85-95.
Jayanth Panyam and Vinod Labhasetwar, Advanced Drug Delivery Reviews, vol. 55, 3, 2003, pp. 329-347.
Lim, Y-b., Kim, C-h., Kim K., Kim S. W., Park, J-s. J. Am., Chem., Soc. 2000, 122, 6524-6525.
M.X. Tang, F.C. Szoka, Gene Ther. 4, 1997, 823-832.
M.X. Tang, C.T. Redemann, F.C. Szoka; Bioconjugate Chem., 1996, 7, 703-714.
Miller, A. D. Angew. Chem. Int. Ed. 1998, 37, 1768-1785.
Niren Murthy, Yi X. Thng, Stephany Schuck, Ming C. Xu, and Jean M. J. Frechet, J. Am. Chem. Soc. 2002, 124, 12398-12399.
Omayra L. Padilla De Jesus, Henrik R. Ihre, Lucie Gagne, Jean M. J. Frechet, and Francis C. Szoka, Jr. Bioconjugate Chem. 2002, 13, 453-461.
R. Langer, N.A. Peppas, Science 263, 1994, 1715-1720.
S.-O. Han, R.I. Mahato, Y.K. Sung, S.W. Kim, Mol. Ther. 2 (4) 2000, 302-317.
Sara-Kaye Madsen and David J. Mooney, Pharmaceutical Science & Technology Today, vol. 3, 11, 2000, pp. 381-384.
W. T. Godbey and A. G. Mikos, Journal of Controlled Release, vol. 72, 1-3, 2001, pp. 115-125.
Wagner, E., Cotton, M., Foisner, R., Birnstiel, M. L. Proc. Natl. Acad. Sci. USA 1991, 88, 4255-4259.
Zabner, J., Fasbender, A. J., Moninger, T., Poellinger, K. A., and Welsh, M. J. (1995) J. Biol. Chem. 270, 18997-19007.
Zhong Zhao, Jun Wang, Hai-Quan Mao and Kam W. Leong, Advanced Drug Delivery Reviews, vol. 55, 4, 2003, pp. 483-499.
Akinc, Akin et al., "Parallel Synthesis and Biophysical Characterization of a Degradable Polymer Library for Gene Delivery," J. Am. Chem. Soc. 2003, 125, pp. 5316-5323.
Jon, Sangyong et al., "Degradable Poly(amino alcohol esters) As Potential DNA Vectors with Low Cytotoxicity," Biomacromolecules 2003, 4, pp. 1759-1762.
Lynn, David M. et al., "Accelerated Discovery of Synthetic Transfection Vectors: Parallel Synthesis and Screening of a Degradable Polymer Library," J.Am. Chem. Soc. 2001, 123, pp. 8155-8156.
Lim, et al., *Cationic Hyerbranched Poly(amino ester)* Journal of American Chemical Society, vol. 123, 2001 pp. 2460-2461.
International Search Report for PCt application No. PCT/US2005/033274, mailed on Mar. 22, 2006.
Written Opinion for PCT application No. PCT/US2005/033274, mailed on Mar. 22, 2006.

* cited by examiner

*Primary Examiner*—Scott D. Priebe
*Assistant Examiner*—Michael Burkhart
(74) *Attorney, Agent, or Firm*—Knobbe, Martens, Olson & Bear, LLP

(57) ABSTRACT

A synthetic polymer comprises a cationic recurring unit and a crosslinking unit, wherein the crosslinking unit comprises at least a first degradable unit (preferably acid-labile) and at least a second degradable unit (preferably hydrolyzable). A carrier composition comprising the synthetic polymer and a bioactive agent is useful for the delivery of the bioactive agent into the nuclei of the cells.

19 Claims, 7 Drawing Sheets

Pentaethylenehexamine:

Linear polyethylenimine:

Branched polyethylenimine (Mw=600)
Branched polyethylenimine (Mw=1200)

N,N'-Bis(2-aminopropyl)-ethylenediamine:

Spermine:

Spermidine:

N-(3-aminopropyl)-1,3-propanediamine:

N,N'-Bis(2-aminoethyl)-1,3-propanediamine:

N-(2-aminoethyl)-1,3-propanediamine:

1-(2-Aminoethyl)piperazine:

1,4-Bis(3-aminopropyl) piperazine:

Tri(2-aminoethyl)amine:

CATIONIC POLYMERS HAVING DEGRADABLE CROSSLINKS

BACKGROUND OF THE INVENTION

1. Field of the Invention

This invention relates generally to degradable polymers. More particularly, the invention relates to crosslinked cationic polymers in which the crosslinks are degradable under physiological conditions. Preferred degradable cationic polymers are useful for delivering bioactive materials (such as nucleic acids) into the nuclei of cells.

2. Description of the Related Art

Gene therapy involves the delivery of nucleic acids (such as DNA) to the nuclei of cells. Both viral and non-viral delivery systems have been developed (1–5). Advantages of non-viral delivery systems include nonimmunogenicity, low acute toxicity, and design flexibility (6–10). A variety of materials have been developed as non-viral gene carriers, including cationic lipids and liposomes (11), endosomal lysis peptides (12), and polymers such as poly-L-lysine (PLL) and its conjugates (13), polyethyleneimine (PEI) (14), polyamidoamine (PAMAM) dendrimers (15), and poly[α-(4-aminobutyl)-L-glycolic acid] (PAGA) (16).

Non-viral gene delivery systems typically function by: (a) formation of a complex between the gene carrier and a nucleic acid, (b) uptake of the complex by cells via endocytosis, (c) escape of the nucleic acid from the endosomes, and (d) entry of the nucleic acid into the nuclei (23). Biodegradable polymer gene carriers have been developed to reduce any potential cytotoxicity of the gene carrier that remains (17–22). However, existing biodegradable polymer gene carriers suffer from a number of shortcomings. For example, such carriers often tend to degrade too slowly (thus risking damage to tissue) or remain inside the cytoplasm for only a short time, resulting in incomplete delivery of the nucleic acid.

REFERENCES

1. Zhong Zhao, Jun Wang, Hai-Quan Mao and Kam W. Leong, Advanced Drug Delivery Reviews, Volume 55, 4, 2003, Pages 483–499.
2. Jayanth Panyam and Vinod Labhasetwar, Advanced Drug Delivery Reviews, Volume 55, 3, 2003, Pages 329–347.
3. Feng Liu and Leaf Huang, Journal of Controlled Release, Volume 78, 1–3, 2002, Pages 259–266.
4. W. T. Godbey and A. G. Mikos, Journal of Controlled Release, Volume 72, 1–3, 2001, Pages 115–125.
5. Sara-Kaye Madsen and David J. Mooney, Pharmaceutical Science & Technology Today, Volume 3, 11, 2000, Pages 381–384.
6. S.-O. Han, R. I. Mahato, Y. K. Sung, S. W. Kim, Mol. Ther. 2 (4) 2000, 302–317.
7. A. Kabanov, Pharm. Sci. & Tech. Today, 2 (9), 1999, 365–372.
8. J.-S. Remy, B. Abdallah, M. A. Zanta, O. Boussif, J.-P. Behr, B. Demeneix, Adv. Drug Delivery Rev. 30, 1998, 85–95.
9. M. X. Tang, F. C. Szoka, Gene Ther. 4, 1997, 823–832.
10. C-H. Ahn, S. Y. Chae, Y. H. Bae, S. W. Kim, J. Controlled Release, 80, 2002, 273–282.
11. Miller, A. D. Angew. Chem. Int. Ed. 1998, 37, 1768–1785.
12. Curiel, D. T., Agarwal, S., Wagner, E., Cotton, M. Proc. Natl. Acad. Sci. USA 1991, 88, 8850–8854.
13. Wagner, E., Cotton, M., Foisner, R., Birnstiel, M. L. Proc. Natl. Acad. Sci. USA 1991, 88, 4255–4259.
14. Boussif, O., Lezoualc'h, F., Zanta, M. A., Mergny, M. D., Scherman, D., Demeneix, B., and Behr, J.-P. Proc. Natl. Acad. Sci. USA 1995, 92, 7297–7301.
15. Haensler, J., and Szoka, F. C., Jr. Bioconjugate Chem. 1993, 4, 372–379. Tang, M. X., Redemann, C. T., and Szoka, F. C., Jr. Bioconjugate Chem. 1996, 7, 703–714.
16. Lim, Y-b., Kim, C-h., Kim K., Kim S. W., Park, J-s. J. Am., Chem., Soc. 2000, 122, 6524–6525.
17. B. M. Jeong, Y. K. Choi, Y. H. Bae, G. Zentner, S. W. Kim, J. Controlled Release 60, 1999, 109–114.
18. B. M. Jeong, D. S. Lee, Y. H. Bae, S. W. Kim, Nature 388, 1997, 860–862.
19. R. Langer, N. A. Peppas, Science 263, 1994, 1715–1720.
20. Omayra L. Padilla De Jesus, Henrik R. Ihre, Lucie Gagne, Jean M. J. Frechet, and Francis C. Szoka, Jr. Bioconjugate Chem. 2002, 13, 453–461.
21. Henrik R. Ihre, Omayra L. Padilla De Jesus, Francis C. Szoka, Jr. and Jean M. J. Frechet, Bioconjugate Chem. 2002, 13, 443–452.
22. Niren Murthy, Yi X. Thng, Stephany Schuck, Ming C. Xu, and Jean M. J. Frechet, J. AM. CHEM. SOC. 2002, 124, 12398–12399.
23: Zabner, J., Fasbender, A. J., Moninger, T., Poellinger, K. A., and Welsh, M. J. (1995) J. Biol. Chem. 270, 18997–19007.

SUMMARY OF THE INVENTION

A preferred embodiment provides a synthetic polymer comprising a cationic recurring unit and a crosslinking unit, wherein the crosslinking unit comprises at least a first degradable unit selected from the group consisting of acetal, imine and hydrazone, and at least a second degradable unit selected from the group consisting of ester, phosphoester, amide, anhydride and urethane. Preferably, the first degradable unit is acid-labile and the second degradable unit is biodegradable (e.g., hydrolyzable). This invention is not bound by theory, but it is believed that the incorporation of at least a first degradable unit and at least a second degradable unit into a single polymer structure allows the polymer to undergo fast degradation in both endosome and cytoplasm environments.

Another preferred embodiment provides a carrier composition comprising the synthetic polymer described above and a bioactive agent selected from the group consisting of nucleic acid, polypeptide, peptide, lipid and carbohydrate. Another preferred embodiment provides a method of delivering a bioactive agent comprising contacting a viable cell with this carrier composition under conditions effective to maintain cell viability.

These and other embodiments are described in greater detail below.

BRIEF DESCRIPTION OF THE DRAWINGS

These and other aspects of the invention will be readily apparent from the following description and from the appended drawings, which are meant to illustrate and not to limit the invention, and wherein.

DETAILED DESCRIPTION OF THE PREFERRED EMBODIMENTS

A preferred embodiments is directed to a synthetic polymer comprising a cationic recurring unit and a crosslinking unit. The term "cationic recurring unit" is used herein in its usual sense to refer to various positively charged chemical groups incorporated into, or suitable for incorporation into, the synthetic polymer, e.g., in the polymer backbone or in a sidechain. Preferred cationic recurring units comprise an amine group that is positively charged. Positively charged amine groups include primary, secondary and tertiary amines that are positively charged under acidic conditions, as well as quaternary amines that are positively charged over a broad pH range. Most preferably, cationic recurring units comprise a quaternary amine group. Poly(amidoamine) dendrimer, polyethylenimine, and polypropylenimine are non-limiting examples of preferred synthetic polymers comprising a cationic recurring unit.

Figure 7:
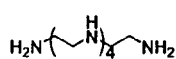
FIG. 7 shows the names and chemical structures of examples of preferred cationic recurring units as well as preferred monomers that may be polymerized to form cationic recurring units.
Figure 7:
Figure 7:
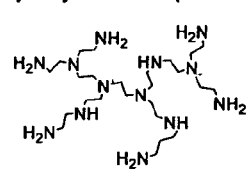
Figure 7:
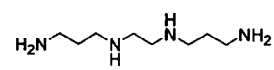
Figure 7:
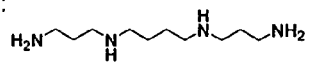
Figure 7:
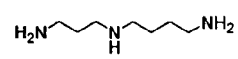
Figure 7:
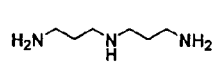
Figure 7:
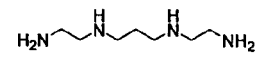
Figure 7:
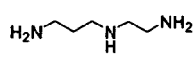
Figure 7:
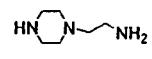
Figure 7:
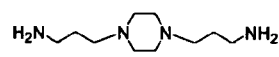
Figure 7:
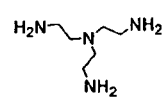

Cationic recurring units may be incorporated into the polymer by polymerization of the corresponding cationic monomers or by post-reaction. Polymerization may be copolymerization and may proceed by various polymerization mechanisms, using techniques generally known to those skilled in the art, including step and chain polymerization mechanisms, see G. Odian, Principles of Polymerization $3^{rd}$ Ed., John Wiley (1991). Non-limiting examples of preferred cationic monomers suitable for polymerization include spermine, spermidine, pentaethylenehexamine, N-(2-aminoethyl)-1,3-propanediamine, N-(3-aminopropyl)-1,3-propanediamine, tris(2-aminoethyl)amine, N,N'-bis(2-aminoethyl)-1,3-propanediamine, N,N'-bis(2-aminopropyl)ethylenediamine, N,N'-bis(2-aminopropyl)-1,3-propanediamine, 1-(2-aminoethyl)piperazine, 1,4-bis(3-aminopropyl)piperazine, and poly(amidoamine) dendrimer. The names and chemical structures of examples of preferred cationic recurring units as well as preferred monomers that may be polymerized to form cationic recurring units are shown in FIG. 7. Cationic monomers may be obtained commercially or synthesized by methods known to those skilled in the art.

Crosslinked polymers contain polymer chains that are attached to one another at points other than their ends, see G. Odian, Principles of Polymerization $3^{rd}$ Ed., John Wiley (1991). As used herein, the term "crosslinking unit" refers to a chemical group that forms part or all of the attachment point between the two chains. Thus, a crosslinking unit is attached to two or more polymer chains at a location other than the ends of the chains. Crosslinking units may be incorporated into the polymer chain by forming the polymer in the presence of a suitable crosslinking agent or by reacting polymers with one another to form attachment points.

The crosslinking unit preferably comprises at least a first degradable unit selected from the group consisting of acetal, imine and hydrazone, and at least a second degradable unit selected from the group consisting of ester, phosphoester, amide, anhydride and urethane. The first degradable unit is preferably acid-labile, and the second degradable unit is preferably hydrolyzable. Preferred crosslinking agents typically include polymerizable groups suitable for reacting with the monomers to result in attachment of the resulting polymer and crosslinking unit to one another. Preferred crosslinking agents may also include the first and second degradable units described above, or the degradable units may be formed by post-reacting the crosslinking unit formed by incorporation of the crosslinking agent into the polymer. Preferred crosslinking agents are represented by the formula $R^1{}_x$—(—X—$R^3$—Y—)$_z$—$R^2{}_y$, where $R^1$ and $R^2$ are polymerizable groups, $R^3$ is a linking group, X is a first degradable unit selected from the group of acetal, imine and hydrazone, Y is a second degradable unit selected from the group consisting of ester, phosphoester, amide, anhydride, and urethane, x and y are integers in the range of 1–3, and z is an integer in the range of 1 to 5. Preferably, $R^1$ and $R^2$ are each independently selected from the group consisting of acrylate, methacrylate, acrylamide, isothiocyanate, isocyanate, epoxide, aldehyde, acyl chloride, sulfonyl chloride, anhydride, maleimide, carboxylic acid, carboxylic acid ester, hydroxyl, amine, and amide. Preferably, $R^3$ is selected from the group consisting of aryl having from 6 to 10 carbons, cycloalkyl having from 4 to 10 carbons, —$(CH_2)_n$—, —$(CH_2O)_n$—, and —$(CH_2CH_2$—O$)_n$—, where n is in the range of 1 to about 100, more preferably in the range of 1 to about 5. Crosslinking agents may be obtained from commercial sources or synthesized by methods known to those skilled in the art, depending on the nature of the groups to be included, e.g., polymerizable groups, first degradable group and second degradable group.

Synthetic polymers comprising a cationic recurring unit and a crosslinking unit are preferably prepared by polymerizing a cationic monomer in the presence of a crosslinking agent. Various polymerization methods may be used, depending on the nature of the polymerizable groups in the monomer and crosslinking agent. In a preferred embodiment, the cationic monomer is an aliphatic, alicyclic or aromatic hydrocarbon bearing two or more active hydrogens such that the monomer is capable of reacting with a suitable crosslinking agent. Polyamines such as those depicted in FIG. 7 are examples of preferred cationic monomers bearing active amine hydrogen atoms. Preferred cationic monomers comprise three or more active hydrogens.

Figure 1:
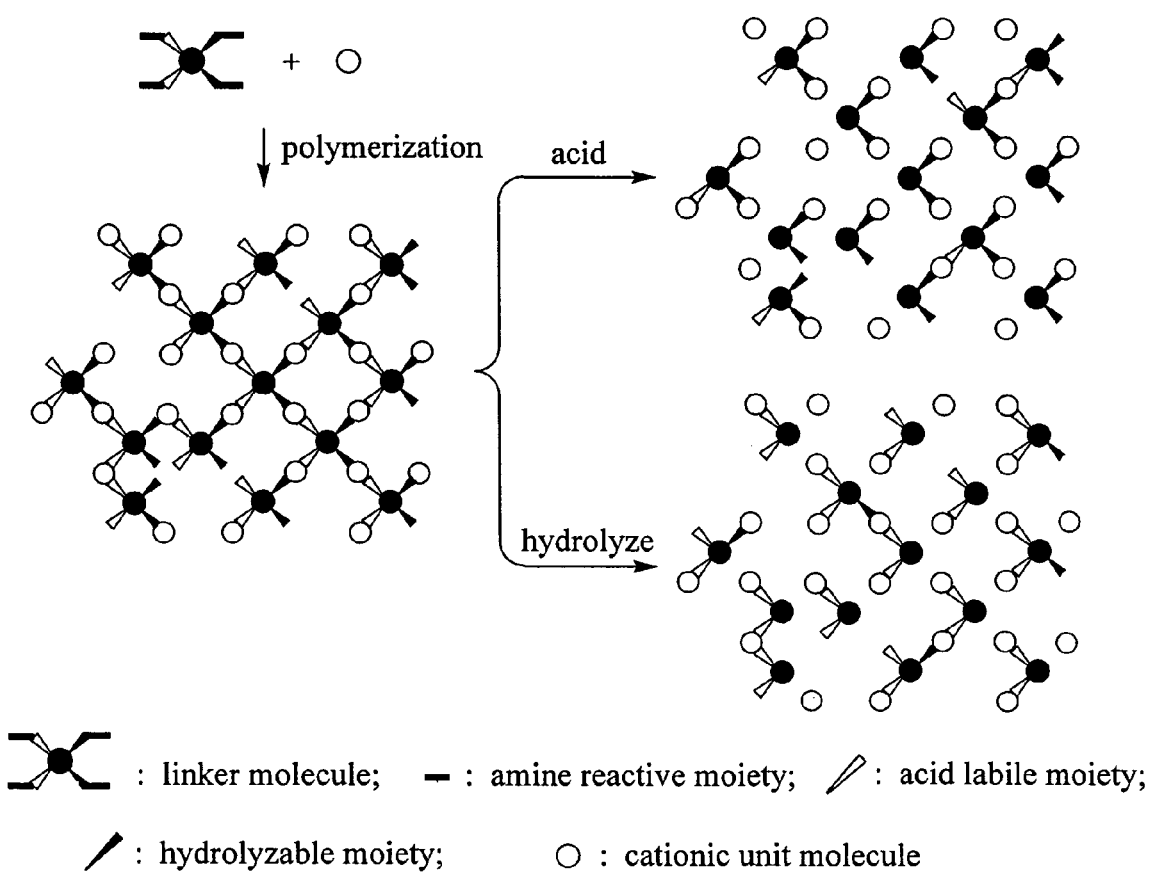
FIG. 1 schematically illustrates examples of polymer synthesis and degradation.

A schematic illustration of the preparation of a synthetic polymer comprising a cationic recurring unit and a crosslinking unit is shown in FIG. 1. The synthesis of a polymer which is derived from pentaethylenehexamine (PEHA) and the crosslinking agent BDADPTA is described in the working examples below and serves as a guide for other synthetic procedures involving similar compounds which can be used to synthesize various cationic polymers. Polymerization of cationic monomers in the presence of a crosslinking agent is preferably carried out in a suitable solvent or suspending medium. The proportions of cationic monomer and crosslinking agent are not critical and may be determined by routine experimentation. For polyamine monomers, the reactant ratio (expressed as the number of amine-reactive functional group equivalents in the crosslinking agent to the number of amine hydrogen equivalents in polyamine monomer) is preferably in the range of from about 1:10 to about 1:1. More preferably, a reactant ratio in the range of from about 1:5 to about 4:5 is employed. For crosslinking agents represented by the formula $R_{1x}$—(—X—$R^3$—Y—$)_z$—$R^2_y$, the number of amine-reactive functional group equivalents is equal to x+y. For polyamines such as those depicted in FIG. 7, the number of amine hydrogen equivalents is the number of reactive hydrogen atoms bonded to the nitrogen atoms.

Another preferred embodiment in directed to a carrier composition comprising the synthetic polymer described above and a bioactive agent selected from the group consisting of nucleic acid, polypeptide, peptide, lipid and carbohydrate. A "nucleic acid" is a polymer containing at least two nucleotides. A "nucleotide" contains a sugar deoxyribose (in DNA) or ribose (in RNA), a base, and a phosphate group. Nucleotides are linked together through the phosphate groups, and they are the monomeric units of nucleic acid polymers. The term nucleic acid includes deoxyribonucleic acid ("DNA") and ribonucleic acid ("RNA"). DNA may be in the form of anti-sense, plasmid DNA, parts of a plasmid DNA, vectors, expression cassettes, chimeric sequences, chromosomal DNA, or derivatives of these groups. RNA may be in the form of oligonucleotide RNA, tRNA, snRNA, rRNA, mRNA, anti-sense RNA, ribozymes, chimeric sequences, or derivatives of these groups.

A "peptide" is a natural or synthetic compound containing two or more amino acids linked by the carboxyl group of one amino acid and the amino group of another. The class of peptides includes many hormones, antibiotics, and other compounds that participate in the metabolic functions of living organisms. "Polypeptide" refers to a linear series of amino acid residues connected to one another by peptide bonds between the alpha-amino group and carboxyl group of contiguous amino acid residues. "Lipids" are a diverse group of biological substances made up primarily or exclusively of nonpolar groups. As a result of their nonpolar character, lipids typically dissolve more readily in nonpolar solvents such as acetone, ether, chloroform, and benzene, than in water. This solubility characteristic is of extreme importance in cells because lipids tend to associate into nonpolar groups and barriers, as in the cell membranes that form boundaries between and within cells. Besides having important roles in membranes, lipids are stored and used in cells as an energy source.

"Carbohydrate" is a term for a large class of polyhydroxylated aldehydes and ketones, with a general formula of $C_x(H_2O)_x$. Aldehydes and ketones both contain a carbonyl group. In ketones both atoms attached to the carbonyl group are carbons whereas in aldehydes one is a hydrogen.

Another preferred embodiment is a carrier composition comprising a crosslinked cationic polymers as described herein and a bioactive agent. Preferred crosslinked cationic polymers have the property, when dispersed in water, of associating strongly via their cationic portions with negatively charged bioactive agents, preferably plasmid or oligonucleotide DNA, to thereby compact the bioactive agents, thereby forming a carrier composition comprising the crosslinked cationic polymer and the bioactive agent. On a charge ratio basis, the carrier composition preferably comprises an excess of crosslinked cationic polymer relative to the nucleic acid, thus facilitating adsorption of the carrier composition on cell membranes and uptake of the bioactive agent by the cells.

Another embodiment is directed to a method of delivering a bioactive agent, comprising contacting a viable cell with the carrier composition described above, under conditions effective to maintain cell viability. In vitro transfection (delivering a bioactive agent into the nuclei of cells) is preferably carried out by bringing a cell suspension into contact with a transfecting mixture obtained, preferably at the time of use, from a solution of the carrier composition described above, in a suitable medium. The transfection time is typically in the range of about 10 minutes to about 48 hours, depending on the nature of the cells.

A preferred in vitro transfection protocol is as follows: cells are seeded at a density of 10,000 cells/well in 96-well plate and grown in minimal essential medium (MEM) supplemented with 10% fetal bovine serum (FBS), 2 mM L-glutamine, 0.1 mM nonessential amino acids, and 1.0 mM sodium pyruvate to reach 60–70% confluence prior to transfection. Before transfection, cells are rinsed and serum-free or 10% FBS-containing medium are added to each well. The cells are treated with a solution containing the carrier complex and 1 μg of plasmid DNA for 4 hours at 37° C. The concentration of cationic polymer is typically varied over a range of polymer/DNA ratios. The transfection mixture is replaced with fresh medium and the cells are further incubated for 48 hours at 37° C.

Luciferase gene expression is preferably measured by a luminescence assay. The growth medium is removed, and the cells are rinsed twice with PBS and lysed for 20 min at room temperature in 100 μL of Reporter Lysis Buffer (Promega). The lysate is cleared by centrifugation, and protein content is determined by using Micro BCA Protein Assay Reagent Kit (Pierce). Thirty microliters of the lysate are dispensed into a luminometer tube, and luciferase activity is integrated over 10 seconds with 2 second measurement delay in a Lumat LB 9507 luminometer (Berthold, Germany) with automatic injection of 100 μL of Luciferase Assay Reagent (Promega). Results are expressed as relative light units per mg of cellular protein.

In vivo studies are generally conducted on mice or rabbits via intravenous administration to determine the biodistribution and kinetics of blood clearance of the injected naked DNA or carrier composition. Cell viability is the ratio of the number of living cells, treated with the carrier composition in PBS buffer solution, vs. the number of living cells treated with PBS only. Evaluation of cell viability is preferably performed by MTT assay: Cell viability (%)=($OD_{sample}$/$OD_{control}$)×100, where $OD_{sample}$ represents the optical density (OD) measurement at 570 nm from the wells treated with the carrier composition, and $OD_{control}$ from the wells treated with PBS buffer solution only. See T. Mosman, "Rapid colorimetric assay for cellular growth and survival:

application to proliferation and cytotoxicity assay" J. Immunol. Methods, 1983, 65, 55–63.

By incorporating both hydrolyzable and acid-labile properties into a single polymer structure, as described in preferred embodiments herein, the degradation process may be controlled by utilizing a combination of both features, e.g., allowing for controlled degradation of the polymer after the controlled delivery of the bioactive agent. This invention is not bound by theory, but it is believed that the degradation begins inside the endosome where the relatively low pH value (pH=5.0–5.5) results in the cleavage of acid-labile bonds and the release of the bioactive agent, followed by hydrolytic degradation of the remaining polymer in the cytoplasm environment, resulting in small molecule components which are preferably nontoxic.

Carrier compositions comprising acid-labile linkages are particularly useful for delivering active substance to certain cells (tumor cells and the like) where the relatively low pH value accelerates the degradation of the polymer. Preferred compositions are relatively simple to prepare and scale up. In addition, numerous non-toxic small molecules containing amine groups may be selected as the initial components, so that the final degradation end molecules are non-toxic.

EXAMPLE 1

Synthesis of Crosslinking Agent (BDADPTA)

Step A: Formation of benzo-1,4-diacetal Dipentaerythritol (BDADP)

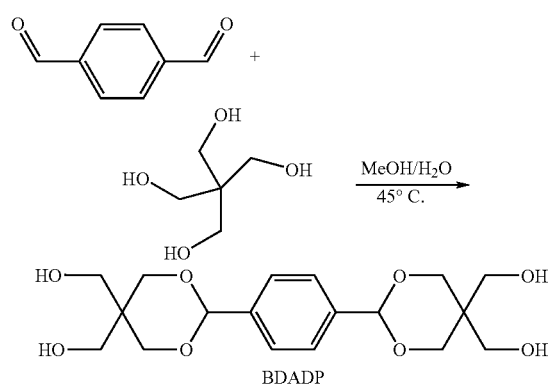

1,4-Dibenzaldehyde (10.0 grams) was dissolved in 125 ml of methanol in a 500 ml round bottom flask and heated to 45° C. Separately, 25.0 grams (g) of pentaerythritol was dissolved in 250 ml of 50:50 methanol/water at 45° C. The solution of pentaerythritol was then added dropwise to the 1,4-dibenzaldehyde solution at 45° C. over 1 hour under stirring. The reaction mixture was allowed to stir for 4 hours at 45° C. A white precipitate formed during the period, which was hot filtered (45° C.) and washed with aqueous $NaHCO_3$. The collected crude product was purified from the starting pentaerythritol by heating to 70° C. in 200 ml of $NaHCO_3$—$H_2O$ solution for 1 hour and hot filtered. The wet water-containing product was then dried by refluxing with toluene over a Dean-Stark water trap, following by filtration after cooled to room temperature. 18 g (65%) product was collected as white solid.

Step B: Formation of benzo-1,4-diacetal dipentaerythritol tetraacrylate (BDADPTA)

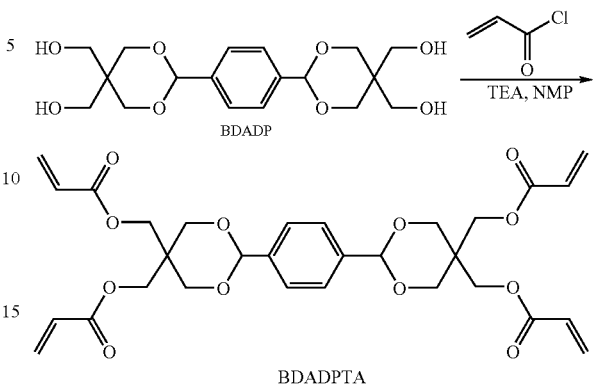

BDADP (25 grams) was dissolved in 500 ml of 1-methyl-2-pyrrolidinone (NMP) at 70° C. in a 1 L 3-neck round bottom flask equipped with two dropping funnels. The system was flushed with argon and the solution was cooled in an ice bath. Triethylamine (TEA, 25 grams) in 25 ml of NMP was added dropwise, following by adding dropwise 42 g of acryolyl chloride in 25 mL of NMP at a slightly slower rate than the TEA to ensure the resulting solution is basic. After the addition the reaction was allowed to warm to room temperature and stir overnight. The NMP was removed by precipitating the reaction mixture into water made basic by $NaHCO_3$. The resulting solid as crude product was then dissolved in DCM, dried over $MgSO_4$, and purified via flash chromatography ($SiO_2$, ethyl acetate/hexane: 10/90). The product was collected as colourless solid (22.0 g, 56%).

EXAMPLE 2

Preparation of crosslinked cationic polymer: 0.46 g of pentaethylenehexamine (PEHA) (from Aldrich) was weighed and placed in a small vial, and 5 ml of methylene chloride was added. After the PEHA completely dissolved, 0.58 g of BDADPTA in 2 ml of methylene chloride was added into the PEHA solution in one portion while stirring at room temperature. More methylene chloride was added to the solution to make the total volume about 10 ml. The resulting reaction mixture was stirred for 9 hours at room temperature before it was added into 100 ml of ether. The resulting crosslinked polymer was precipitated and obtained as gel-like solid after centrifuge, followed by drying under reduced pressure. $^1$H-NMR spectrum showed that the acrylic carbon-carbon double bond disappeared completely.

EXAMPLE 3

In vitro transfection efficiency: This example demonstrates that the polymer of Example 2 (Sample 1) is able to deliver plasmid DNA (or other bioactive species) to the nuclei of mammalian cells. This is demonstrated by a transfection efficiency experiment in which the GFP (green fluorescence protein) plasmid DNA was used as a reporter gene.

Figure 2:
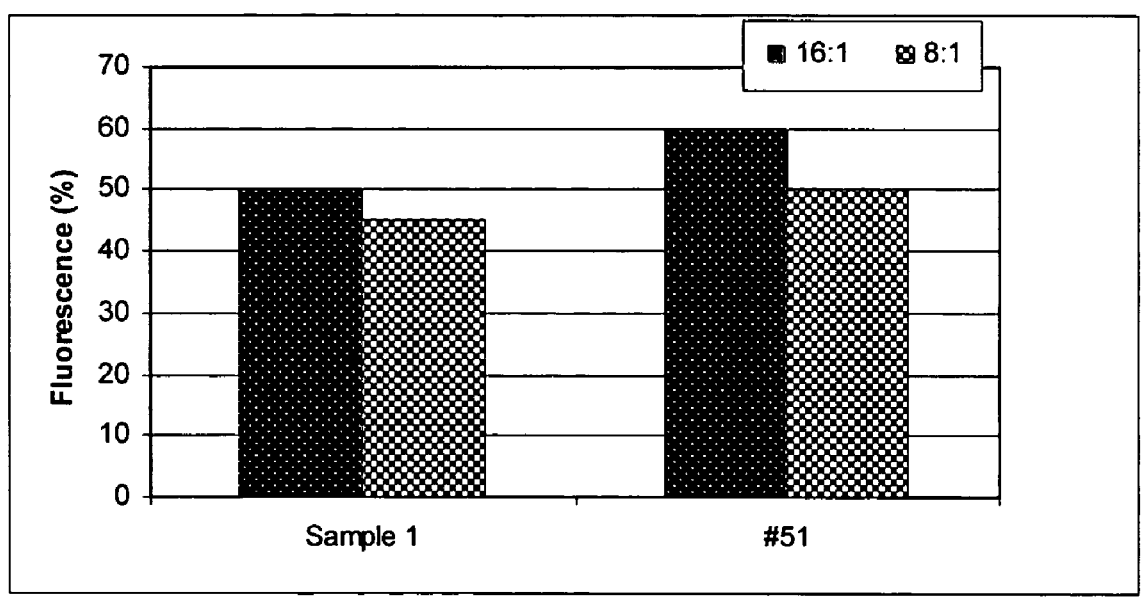
FIG. 2 shows a bar graph illustrating the transfection efficiency of green fluorescent protein (GFP) reporter gene delivered into 293 cells by a preferred cationic polymer (Sample 1), compared with a standard sample (#51). The GFP signals were observed at 24 hours after transfection. The numbers shown in parentheses indicate the weight ratio of the polymer to DNA.

Procedure: Permanent cells (293 or HT1080 cells, ATCC) were plated in 24-well tissue culture plates (2×10⁵ cells/well for 293 cells and 8×10⁴ cells/well for HT1080) and incubated overnight in DMEM (Gibco) with 10% FBS (Gibco). For each well, an aliquot of 30 μl DMEM containing different amounts of the crosslinked polymer of Example 2, corresponding to DNA/polymer weight ratios of 16/1 and 8/1, was added dropwise into 30–μl DMEM solution containing 0.6 μg of plasmid DNA (pCMV–GFP plasmid DNA)

while vortexing. The polymer-DNA solutions (carrier compositions) were incubated for 15 min. at room temperature to allow the formation of DNA-polymer complexes. 150 µl of DMEM medium containing 10% FBS and antibiotics was added to the DNA-polymer complex, and then the mixture was added to the cells in individual wells after the cells were washed with PBS. Cells were incubated (37° C., 7.5% $CO_2$) for 3 hrs, and then the medium was changed to DMEM medium containing 10% FBS and 100 U/ml Penicillin and 100 µg/ml streptomycin. Twenty-four hours after transfection, GFP signals in cells were observed under a fluorescent microscope (Olympus, filter 515–550 nm). The percentage of cells with GFP signal in transfected cultures was determined from counts of three fields for optimal cationic polymer amounts. The transfection percentages of crosslinked polymers, as shown in FIG. 2, were 50% (16/1) and 45% (8/1), compared with a commercial standard cationic polymer #51 having 60% (16/1) and 50% (8/1) transfection efficiency values.

EXAMPLE 4

Figure 3:
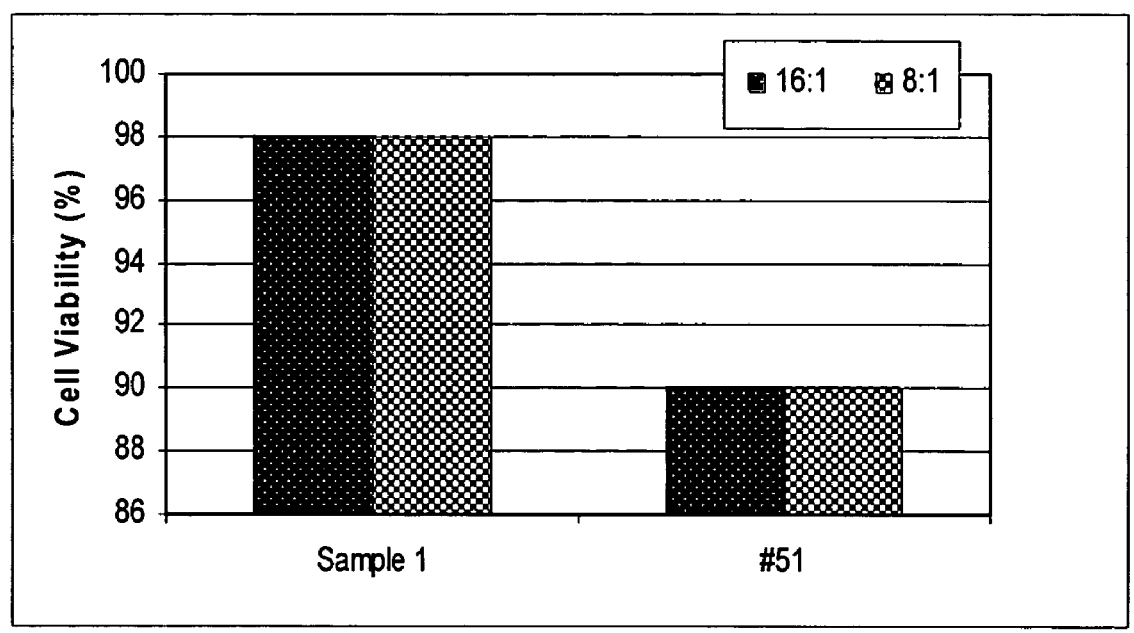
FIG. 3 shows a bar graph illustrating the cell survival percentage (293 cells) after treatment with a series of preferred cationic polymer-DNA complexes (Sample 1), compared with a standard sample (#51). The numbers shown in parenthesis indicate the weight ratio of the polymer to DNA.

Toxicity of the crosslinked polymer to cells: The cytotoxicity of the crosslinked cationic polymer of Example 2 (Sample 1) on mammalian cells was evaluated using a 3-[4,5 dimethylthiazol-2-yl]-2,5-diphenyltetrazolium bromide (MTT) method. Briefly, HT1080 cells, $2\times10^4$ cells/well or $4\times10^4$ 293 cells, were seeded in 96-well plates and incubated for 16–24 hr. An aliquot of 15 µl DMEM, containing the polymer, was added drop by drop into 15 µl DMEM containing 0.3 µg plasmid and incubated at room temperature for 15 min to form polymer/DNA complexes. Seventy-five microliters (75 µl) of DMEM was added to the polymer-DNA complexes, and 50 µl of the mixture was added to the cells and incubated (37° C., 7.5% $CO_2$) for 3 h. The media was then removed and DMEM medium containing 10% FBS and 100 U/ml Penicillin and 100 µg/ml streptomycin were added. Following further incubation for 24 hrs, the media was removed and 10 µl of MTT solution (5.0 mg/ml, Sigma) was added to each well, and incubated for 3 hrs. The medium was then removed and 200 µl DMSO was added to dissolve the formazan crystals. All the experiments were conducted in triplicate. The absorbance of the solution was measured at 570 nm. Cell viabilities was visualized under a fluorescent microscope (Olympus, filter 515–550 nm) and calculated using the equation: Viability (%)={Abs570 (sample)/Abs570 (control)}×100. The results indicated that the cytotoxicity of the crosslinked polymer was significantly lower than the standard NDT cationic polymer as many more cells survived following transfection. The results are shown graphically in FIG. 3 (Sample 1 is crosslinked cationic polymer of Example 2, # 51 is commercial control).

EXAMPLE 5

Figure 4:
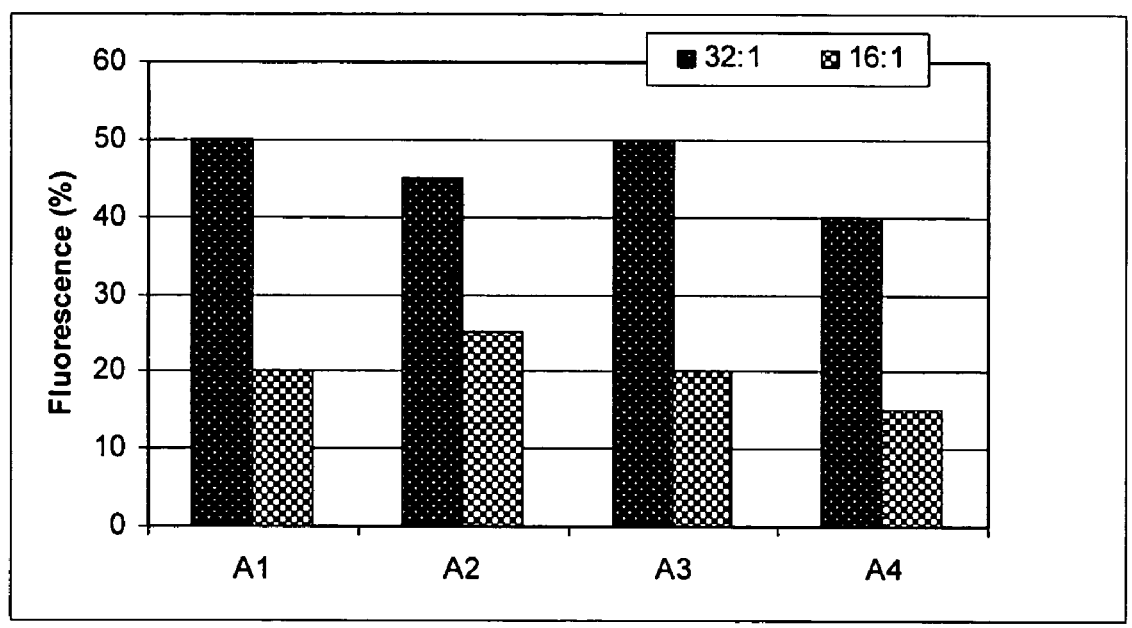
FIG. 4 shows a bar graph illustrating GFP gene transfection efficiency of a preferred cationic polymer (Sample 1), after incubation in PBS buffer solution (pH=7.4) at ambient temperature (~22° C.) for 4 hrs (A1), 8 hrs (A2), 24 hrs (A3), and 48 hrs (A4). The GFP signals were observed at 24 hours after transfection. The numbers shown in parentheses indicate the weight ratio of the polymer to DNA.
Figure 5:
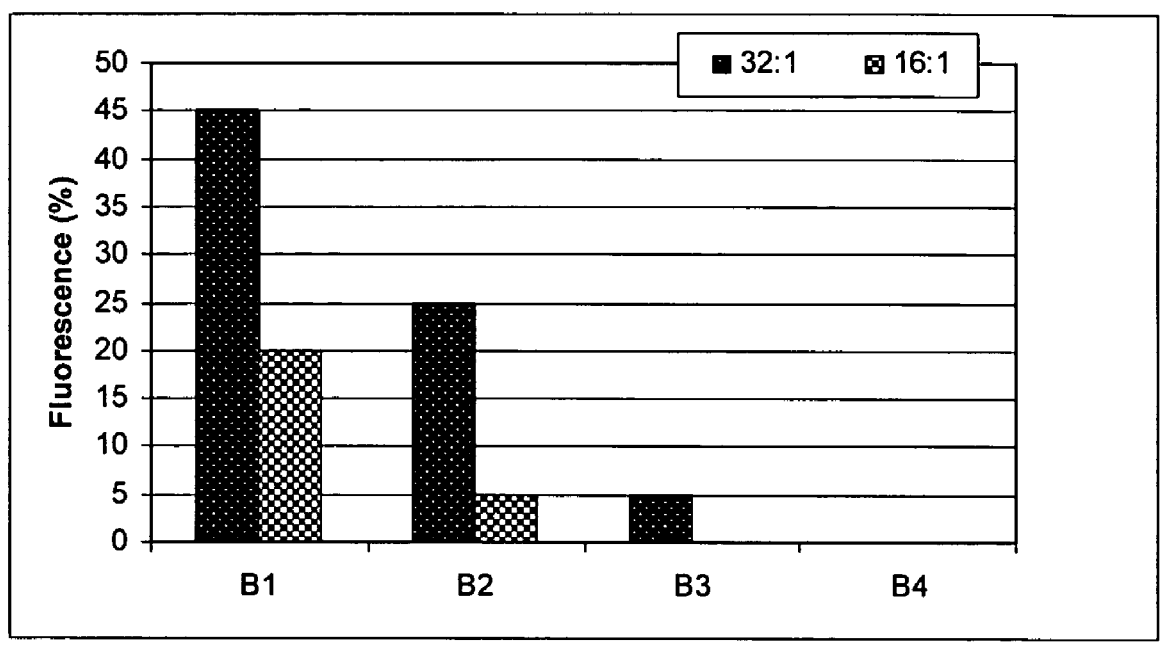
FIG. 5 shows a bar graph illustrating GFP gene transfection efficiency of a preferred cationic polymer (Sample 1), after incubation in PBS buffer solution (pH=7.4) at 37° C. for 4 hrs (B1), 8 hrs (B2), 24 hrs (B3), and 48 hrs (B4). The GFP signals were observed at 24 hours after transfection. The numbers shown in parentheses indicate the weight ratio of the polymer to DNA.
Figure 6:
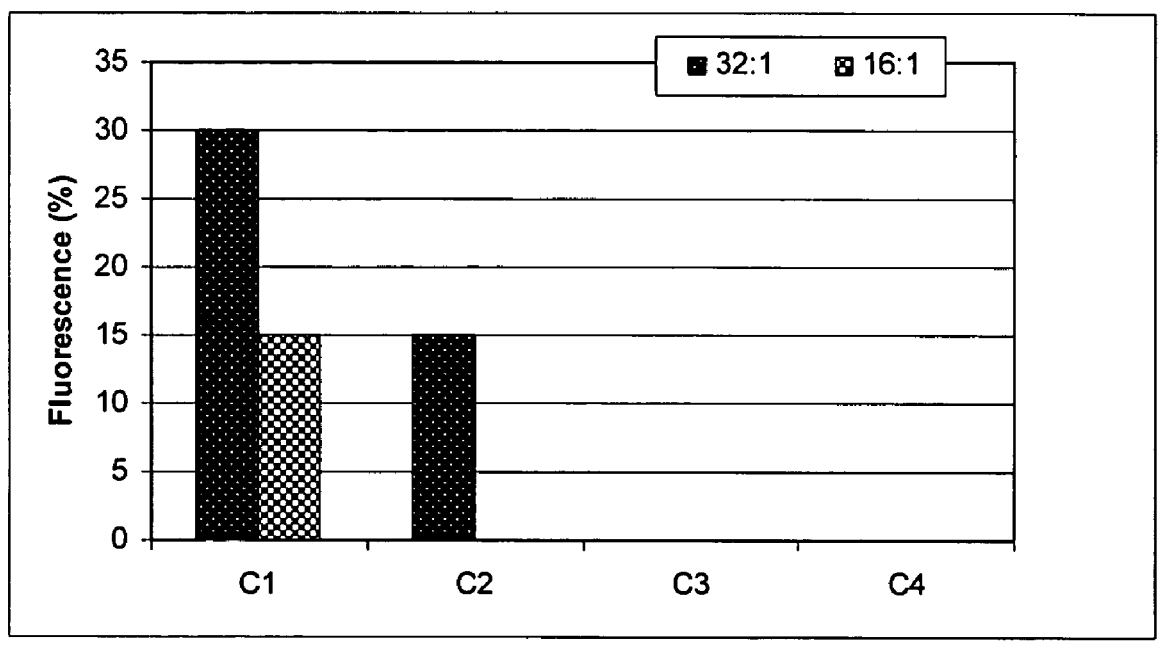
FIG. 6 shows a bar graph illustrating the GFP gene transfection efficiency of a preferred cationic polymer (Sample 1), after incubation in pH=5 buffer solution at ambient temperature (~22° C.) for 4 hrs (C1), 8 hrs (C2), 24 hrs (C3), and 48 hrs (C4). The GFP signals were observed at 24 hours after transfection. The numbers shown in parentheses indicate the weight ratio of the polymer to DNA.

Degradation of the crosslinked polymers in different environments: In order to evaluate the degradation of the crosslinked polymer of Example 2 in different environments, a sample of the crosslinked polymer of Example 2 (Sample 1) was incubated in PBS buffer solution at 5 mg/ml concentration at both ambient temperature (~22° C.) and 37° C. for 4 hrs, 8 hrs, 24 hrs, and 48 hrs, respectively, to evaluate the hydrolytic degradation of the samples under neutral conditions. Samples of the various partially degraded polymers were then evaluated by using a GFP transfection measurement (FIG. 4 and FIG. 5). The same GFP transfection measurement was also performed on the crosslinked polymer of Example 2 after incubation in pH=5 buffer solution at a concentration of 5 mg/ml at ambient temperature (~22° C.) for the same time intervals. In acid, (FIG. 6), the results show that the transfection efficiency quickly decreased as the incubation time increased to 24 hours. Under neutral conditions, however, the sample was more stable (FIGS. 4 and 5). The transfection efficiency from the sample after incubation in PBS at room temperature for 48 hrs still retained 80% of its original value. Accelerated decomposition was observed at elevated temperatures where the transfection efficiency dropped to 10% of its original value after incubation in PBS at 37° C. for 24 hrs.

It will be appreciated by those skilled in the art that various omissions, additions and modifications may be made to the processes and compositions described above without departing from the scope of the invention, and all such modifications and changes are intended to fall within the scope of the invention, as defined by the appended claims.

What is claimed is:

1. A synthetic polymer comprising a cationic recurring unit and a crosslinking unit, wherein the crosslinking unit comprises at least a first degradable unit selected from the group consisting of acetal, imine and hydrazone, and at least a second degradable unit selected from the group consisting of ester, phosphoester, amide, anhydride and urethane.

2. The synthetic polymer of claim 1 in which the cationic recurring unit comprises an amine group or a salt thereof.

3. The synthetic polymer of claim 2 in which the amine group or a salt thereof is a tertiary amine group.

4. The synthetic polymer of claim 1 that is water-swellable.

5. The synthetic polymer of claim 1 having a weight average molecular weight in the range of about 1,000 to about 100,000 Daltons.

6. The synthetic polymer of claim 1 wherein the first degradable unit is acetal.

7. The synthetic polymer of claim 1 wherein the second degradable unit is ester.

8. The synthetic polymer of claim 1 wherein the first degradable unit is acetal and the second degradable unit is ester.

9. A carrier composition comprising the synthetic polymer of claim 1 and a bioactive agent selected from the group consisting of nucleic acid, polypeptide, peptide, lipid and carbohydrate.

10. The carrier composition of claim 9 in which the bioactive agent is a nucleic acid.

11. The carrier composition of claim 10 in which the nucleic acid is selected from the group consisting of DNA, RNA, ribosome and DNA—RNA hybrid.

12. The carrier composition of claim 10 in which the nucleic acid is DNA.

13. The carrier composition of claim 10 in which the nucleic acid is RNA.

14. The carrier composition of claim 13 in which the RNA is double stranded.

15. A method of delivering a bioactive agent comprising contacting a viable cell with the carrier composition of claim 9 under conditions effective to maintain cell viability.

16. The method of claim 15 in which the bioactive agent is DNA.

17. The method of claim 16 in which the first degradable unit of the synthetic polymer is acetal.

18. The method of claim 17 in which the second degradable unit of the synthetic polymer is ester.

19. The method of claim 18 in which the cell is a human cell.

* * * * *